United States Patent [19]

Steer et al.

[11] 4,331,148
[45] May 25, 1982

[54] DEODORIZING OSTOMY BAG COVER

[75] Inventors: Peter L. Steer; John V. Edwards, both of East Grinstead, England

[73] Assignee: Kingsdown Medical Consultants Limited, London, England

[21] Appl. No.: 173,786

[22] Filed: Jul. 30, 1980

[30] Foreign Application Priority Data

May 16, 1979 [GB] United Kingdom ............... 7917129
Aug. 8, 1979 [GB] United Kingdom ............... 7927623

[51] Int. Cl.³ .............................................. A61F 5/44
[52] U.S. Cl. .................................................. 128/283
[58] Field of Search ........................................ 128/283

[56] References Cited

U.S. PATENT DOCUMENTS

| D. 245,119 | 7/1977 | Harris | 128/283 |
|---|---|---|---|
| 2,555,086 | 5/1951 | Guinn | 128/283 |
| 3,439,677 | 4/1969 | Bonfils | 128/283 |
| 3,759,260 | 9/1973 | Nolan et al. | 128/283 |
| 3,804,091 | 4/1974 | Nolan et al. | 128/283 |
| 3,952,727 | 4/1976 | Nolan | 128/283 |
| 4,120,715 | 10/1978 | Ockwell et al. | 128/283 |

FOREIGN PATENT DOCUMENTS

| 1301101 | 12/1972 | United Kingdom . |
|---|---|---|
| 1363644 | 8/1974 | United Kingdom . |
| 1416594 | 12/1975 | United Kingdom . |
| 1541565 | 3/1979 | United Kingdom . |
| 2031282 | 4/1980 | United Kingdom . |

Primary Examiner—Robert W. Michell
Assistant Examiner—T. J. Wallen
Attorney, Agent, or Firm—Lawrence S. Levinson; Stephen B. Davis

[57] ABSTRACT

A deodorizing bag which encloses an ostomy bag. The cover bag is formed of material containing activated carbon or has an area of its inner wall formed of such filtering material.

5 Claims, 8 Drawing Figures

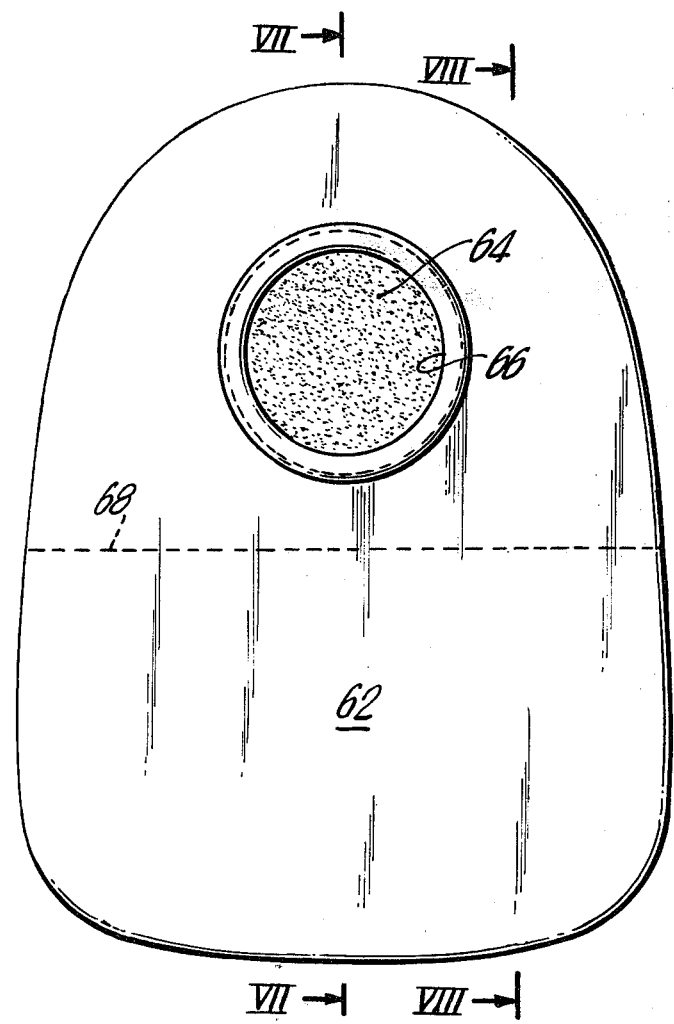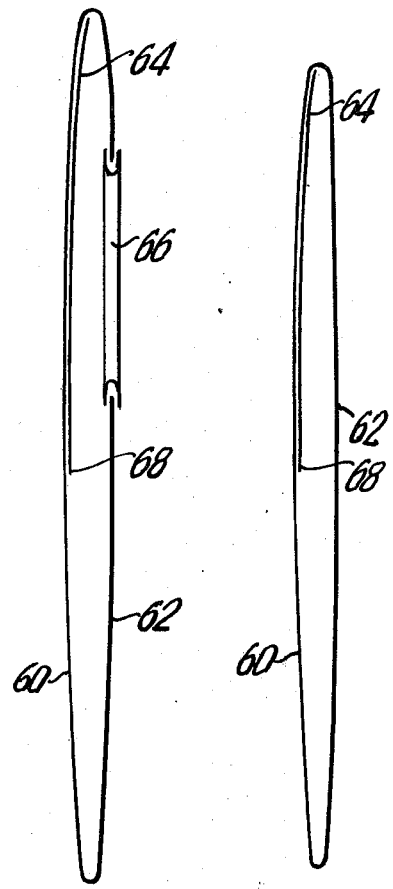
FIG. 6          FIG. 7   FIG. 8

DEODORIZING OSTOMY BAG COVER

BACKGROUND OF THE INVENTION

Most ostomates employ some type of bag or pouch system to collect bodily wastes discharged from their surgically created stoma. Today, such pouches are generally formed of light weight, odor proof, flexible polymeric materials and the collection systems are designed to be inconspicuous and permit the ostomate to engage in normal physical activity. However, many ostomates, particularly immediately following surgery, have fears concerning their ability to resume a "normal" life. These fears center around worries that the collection system will leak or that odor will escape and that the system will be noticeable even through their outer clothing.

In order to decrease the visability of fecal matter within their pouch and prevent clothing from sticking to the pouch many ostomates employ a cover which slips over the pouch. Such covers are generally of cloth material. An example of such a cover is shown by Harris in U.S. Design Pat. No. 245,119.

In order to overcome the problem of flatus billowing out the pouch, it has been suggested that vent openings be provided and also that filtering means be included so as to deodorize the escaping gas. Examples of such devices are shown in U.S. Pat. Nos. 2,555,086; 3,439,677; 3,759,260; 3,804,091; 3,952,727; British Pat. Nos. 1,363,644; 1,416,594; 1,541,565; and British Application No. 2,031,282.

SUMMARY OF THE INVENTION

This invention is directed to a deodorizing cover for an ostomy bag. The term "ostomy bag" is used to mean a colostomy or ileostomy or other kind of bag intended to be worn by a user to receive waste material expelled from the stoma.

According to one embodiment of this invention, there is provided a cover bag for substantially enclosing an ostomy bag. The cover bag is entirely made of filtering material or at least an upper portion of the cover bag is made of such filtering material. The upper portion of the cover bag which is made of filtering material is preferably located on the inner side of that wall of the cover bag which will face away from the wearer in normal use. Alternatively, this upper portion made of filtering material may extend over part of both cover walls.

According to another embodiment of this invention, a cover bag for an ostomy bag is provided with a detachable insert of pouch form that is made of filtering material. The pouch is constructed to fit over the upper region of the ostomy bag.

The filtering material employed in the above described cover bags can be made of a woven or nonwoven material incorporating activated carbon particles or granules therein. It can also be activated fibrous carbon cloth as described in British Pat. No. 1,301,101.

BRIEF DESCRIPTION OF THE DRAWINGS

FIG. 6 is a rear view of a cover bag having a patch of filtering material in an upper region thereof;

FIG. 7 is a diagrammatic cross-section taken on the line VII—VII of FIG. 6; and

FIG. 8 is a diagrammatic cross-section taken on the line VIII—VIII of FIG. 6.

DETAILED DESCRIPTION OF THE INVENTION

The deodorizing cover bags of this invention can be employed with any ostomy bag. However, they are particularly adapted to be used with an ostomy bag that has a coupling member which attaches the bag to a second coupling member adhesively attached to the body of the user. Such a coupling system is described in U.S. patent application Ser. No. 881,274 filed Feb. 27, 1978 which is published as Belgian Pat. No. 865,521.

Figure 1:
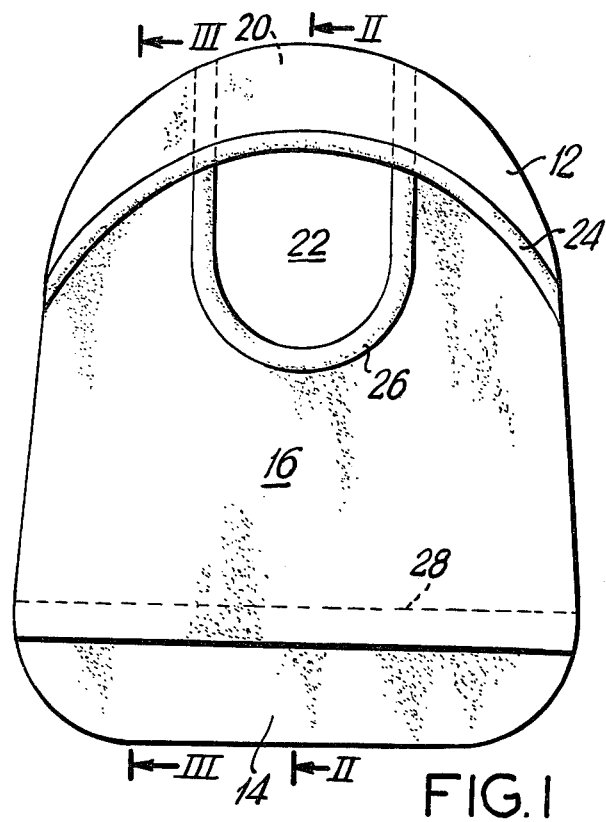
FIG. 1 is a rear view of a cover bag made entirely of filtering material.
Figure 2:
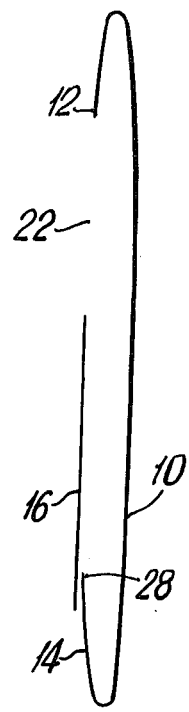
FIG. 2 is a diagrammatic cross-section on the line II—II of FIG. 1.
Figure 3:
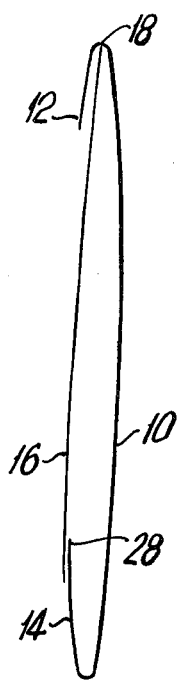
FIG. 3 is a diagrammatic cross-section on the line III—III of FIG. 1.

The cover bag illustrated in FIGS. 1-3 is made wholly of the aforesaid filtering material. This cover bag has a front wall 10 which is contiguous with a top hood wall 12 and a pocket wall 14. It also has a rear wall 16 which is secured to the top edge 18 of the cover bag, note FIG. 3, except over a region 20 which defines a space 22 to accept a coupling member by which the ostomy bag is connected to the user. The pocket defined by the lower part of the front wall 10 and the pocket wall 14 in practical use of the cover bag supports and receives the lower end of the ostomy bag.

This cover bag may be made by conventional sewing techniques, and bias binding or other reinforcement may be included as needed. Bias binding is indicated at 24 and 26 in FIG. 1. The top edge of the pocket wall 14 is indicated at 28. In accordance with sound sewing practice, all unfinished hems are to be located on the inside of the bag cover, and ends of machining runs are to be tied off.

Figure 4:
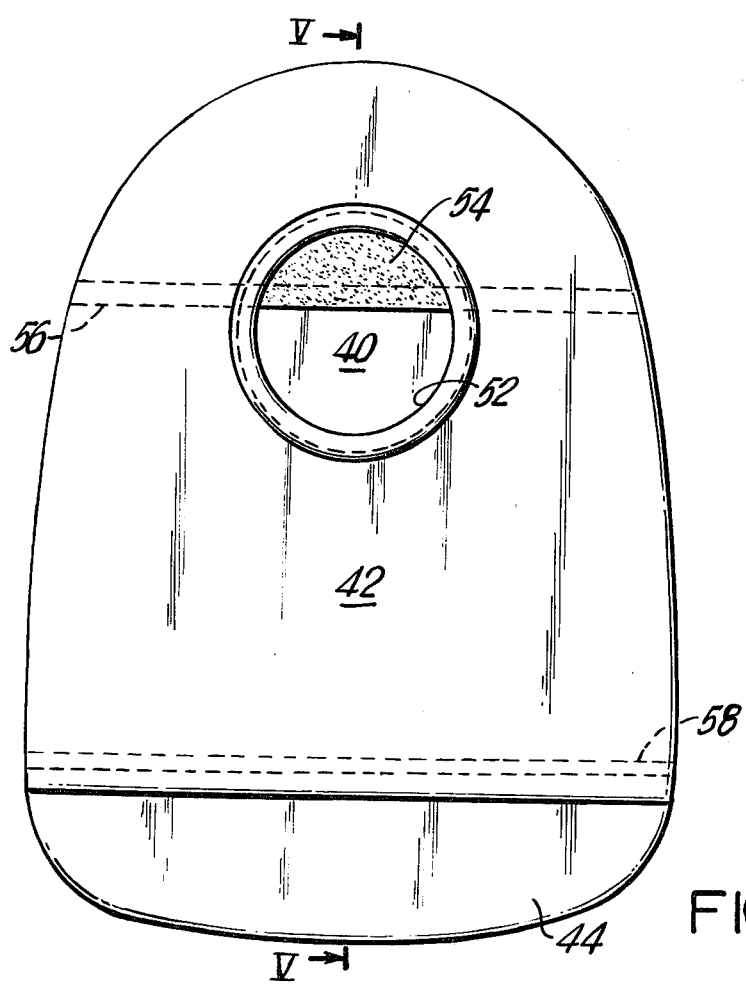
FIG. 4 is a rear view of a cover bag in which the upper portion is made of filtering material.
Figure 5:
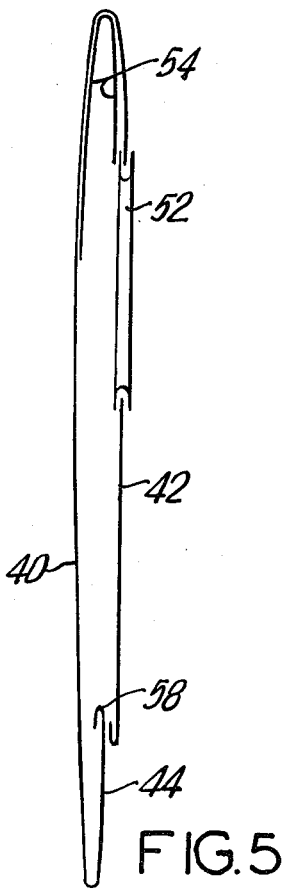
FIG. 5 is a diagrammatic cross-section on the line V—V of FIG. 4.

The cover bag illustrated in FIGS. 4 and 5 has a front wall 40 and a rear wall 42. In the rear wall 42 there is a circular hole 52 which allows passage of the coupling member of the ostomy bag. The front wall 40 is contiguous with a wall 44 that bounds a pocket in the lower portion of the cover bag. At least an upper portion of the cover bag has an area of the aforesaid filtering material. The filtering material is indicated at 54 in FIGS. 4 and 5. The material 54 extends over all the upper portion of the front wall 40, on the inner side of said wall, and extends over that portion of the rear wall above the line 56. The reference numeral 58 indicates the top edge of the pocket wall 44. It will be understood that except for the portion visible through the hole 52, the front wall 40 is not seen in FIG. 4.

While the material 54 has been shown as an insert, which is preferably stitched in place, for example by a line of stitching along the line 56, in other embodiments of the invention the said material 54 could be formed by a readily removable and detachable patch.

Again, this cover bag may be made by conventional sewing techniques, and bias binding or other reinforcement may be included as needed. The top edge of the pocket wall 44 is indicated at 58. As before, all unfinished hems are to be located on the inside of the bag cover, and ends of machining runs are to be tied off.

Referring now to FIGS. 6-8, the illustrated cover bag includes a front wall 60 and a rear wall 62 which are stitched together around their periphery, in accordance with conventional sewing techniques. The upper region of the front wall 60 has a patch of the aforesaid filtering material, said patch being indicated by 64. The rear wall 62 has a hole 66 therein, which is similar in purpose and location to the hole 52 of the embodiment shown in FIGS. 3 and 4. The line 68 in FIG. 6 illustrates the lower boundary of the patch 64, and the patch 64 may be sewn in place by stitching along or parallel to the said line. It may also be held in place by stitching around the upper periphery of the cover bag.

It will be understood that the exact dimensions illustrated are not critical and so long as the cover bag satisfactorily accomodates an ostomy bag therein, any suitable dimensions may be chosen.

In use, when the user fits a new ostomy bag, he or she punctures a hole in the upper region of the ostomy bag which will allow any gases which may accumulate therein to escape. These gases in escaping are obliged to pass through the filtering material of the cover bag and in so doing are largely or wholly deodorized. Such a cover bag is light and easy to wear, and may be easily mass-produced at reasonable cost. Moreover, it avoids the "cold" feel of a plastics bag on the human skin.

What is claimed is:

1. A deodorizing cover bag for substantially enclosing an ostomy bag said cover bag formed of filtering material containing activated carbon and including a front wall having a top edge, a bottom edge, and side edges, a top hood wall secured to said front wall top edge and the upper portions of said front wall side edges, a pocket wall secured to said front wall bottom edge and the lower portions of said front wall side edges, and a rear wall secured to said front wall top edge and said front wall side edges provided that said rear wall is not secured to said front wall top edge over a region which is dimensioned and positioned to permit the enclosed ostomy bag to be coupled to the body of the user, and wherein said rear wall overlaps said pocket wall but is not connected thereto.

2. A deodorizing cover bag for substantially enclosing an ostomy bag including a front wall having a top edge, a bottom edge, and side edges, a pocket wall secured to said front wall bottom edge and the lower portions of said front wall side edges, a rear wall secured to said front wall top edge and said front wall side edges, said rear wall having an opening dimensioned and positioned to permit the enclosed ostomy bag to be coupled to the body of the user, said rear wall overlapping but not connected to said pocket wall, and a patch of activated carbon filtering material sewn into place on the inside of said front wall and extending from said front wall top edge downward along a portion of said front wall.

3. A cover bag according to claim 2 wherein said patch of filtering material also extends from said front wall top edge downward along a portion of said rear wall.

4. A deodorizing cover bag for substantially enclosing an ostomy bag including a front wall having a top edge, a bottom edge, and side edges, a rear wall secured to said front wall top edge, said front wall bottom edge, and said front wall side edges, said rear wall having an opening dimensioned and positioned to permit the enclosed ostomy bag to be coupled to the body of the user, and a patch of activated carbon filtering material sewn into place on the inside of said front wall and extending from said front wall top edge downward along a portion of said front wall.

5. A cover bag according to claim 4 wherein said patch of filtering material also extends from said front wall top edge downward along a portion of said rear wall.

* * * * *